(12) United States Patent
Whitcomb et al.

(10) Patent No.: US 10,853,515 B2
(45) Date of Patent: Dec. 1, 2020

(54) SECURE STORAGE AND ACCESS TO SENSITIVE DATA

(71) Applicant: salesforce.com, inc., San Francisco, CA (US)

(72) Inventors: Wayne Whitcomb, North Hampton, NH (US); David C. Boyle, Austin, TX (US)

(73) Assignee: Salesforce.com, inc., San Francisco, CA (US)

( * ) Notice: Subject to any disclaimer, the term of this patent is extended or adjusted under 35 U.S.C. 154(b) by 796 days.

(21) Appl. No.: 14/486,335

(22) Filed: Sep. 15, 2014

(65) Prior Publication Data

US 2016/0342811 A1 Nov. 24, 2016

(51) Int. Cl.
*G16H 10/60* (2018.01)
*G06F 21/62* (2013.01)
*G06F 16/245* (2019.01)

(52) U.S. Cl.
CPC ........ *G06F 21/6245* (2013.01); *G06F 16/245* (2019.01); *G16H 10/60* (2018.01)

(58) Field of Classification Search
None
See application file for complete search history.

(56) References Cited

U.S. PATENT DOCUMENTS

| | | | |
|---|---|---|---|
| 6,931,532 B1 | 8/2005 | Davis et al. | |
| 6,941,459 B1 | 9/2005 | Hind et al. | |
| 6,948,067 B2 | 9/2005 | Hawkes et al. | |
| 7,320,008 B1 | 1/2008 | Colgrove | |
| 7,325,129 B1 | 1/2008 | Mattsson et al. | |
| 7,376,831 B2 | 5/2008 | Kollmyer et al. | |
| 7,519,835 B2 | 4/2009 | Koyfman | |
| 7,689,547 B2 | 3/2010 | Cristofor et al. | |
| 8,165,305 B2 | 4/2012 | Chrysler et al. | |
| 8,826,019 B2* | 9/2014 | Shablygin | G06F 21/34 713/168 |
| 2004/0204965 A1* | 10/2004 | Gueck | G16H 30/20 705/3 |
| 2005/0004924 A1 | 1/2005 | Baldwin | |
| 2006/0020611 A1* | 1/2006 | Gilbert | G06F 21/6254 |
| 2010/0114781 A1* | 5/2010 | Kassas | G06F 19/322 705/50 |

(Continued)

OTHER PUBLICATIONS

R. Agrawal et al., "Watermarking relational data: framework, algorithms and analysis", The VLDB Journal, 2003, p. 157-169, vol. 12, Springer-Verlag.

(Continued)

*Primary Examiner* — Michael Tomaszewski
(74) *Attorney, Agent, or Firm* — Butzel Long

(57) ABSTRACT

A method and system for securely storing and accessing sensitive user data (e.g., personally identifying information or PII) is described. In an aspect, PII is divided into a plurality of separately stored data stores based on what type or field of PII are collected. Each piece of PII data or PII datum is associated with a unique code so as to form data pairs comprising the PII datum and the unique code associated with that PII datum. A tumbler data structure allows secure association of the unique codes for the PII data for each user. Once the tumbler data structure is unlocked, a provider can search and access the PII data of its users.

5 Claims, 11 Drawing Sheets

(56) References Cited

U.S. PATENT DOCUMENTS

2011/0010563 A1 1/2011 Lee et al.
2011/0047380 A1 2/2011 Miller

OTHER PUBLICATIONS

W. Itani et al., "An Enterprise Policy-Based Security Protocol for Protecting Relational Database Network Objects", 2006, p. 343-348, ACM, Vancouver, British Columbia, Canada.
U. T. Mattsson, "Providing Database Encryption as a Scalable Enterprise Infrastructure Service—Optimizing Performance and Protection for Databases".
S. Evdokimov et al., "Provable Security for Outsourcing Database Operations", Proceedings of the 22nd International Conference on Data Engineering, 2006, p. 1-4, IEEE.
U.S. International Searching Authority, "International Search Report for Application No. PCT/US14/55622", dated Jun. 3, 2015, WIPO.
Extended European Search Report for Application No. 14901838.4, dated Apr. 6, 2018 (8 Pages).

* cited by examiner

SECURE STORAGE AND ACCESS TO SENSITIVE DATA

TECHNICAL FIELD

This invention relates to the storage of and access to sensitive personal information, which may be used to protect the confidentiality of sensitive data and to control access to the data.

BACKGROUND

There is a known need to collect and store data and information, for example personal, financial, demographic and similar information to enable transactions requiring such information. Electronic commercial transactions and a growing number of medical, educational and government services rely on the provision of such sensitive data. Examples abound, for example in the conduct of online commerce in the purchase of products and services over the Internet without the buyer and seller meeting face to face to authenticate or assure the transaction. We generally refer to all types of retailers, institutions, corporations or entities providing services, products or account access herein as "providers." The consumers, clients, customers, buyers, subscribers or beneficiaries receiving the products or services of the providers are referred to herein as "users." In general, both the providers and users in the present context can be individuals, corporations or other entities.

Conventionally, a provider offering products or services requires information concerning the user of its products or services, including for example a user account name or number and a user password. Providers typically collect personal and financial data, or data generally identifying a user that alone or in combination the user would not choose to be known by unauthorized parties, to enable secure transactions and access to their services. We refer to such information and data as personally identifying information (PII), which is commonly of a private nature, including a user's name, address, telephone and email address. This information can include further sensitive data about the user such as the user's credit card numbers, date of birth, social security number, bank account information. Still further, this information sometimes includes very personal and non-public authenticating information concerning the user as an individual to confirm secure access by this person to an online transaction or account. This personal authenticating information can include a user's mother's maiden name, the name of the person's first pet, the color of the user's child's eyes, the make of their first car, city of birth, or other information presumed to prevent access by persons other than an authorized user who has provided such authenticating personal information to the provider.

User information or PII is collected by the providers and stored to facilitate later repeat visits by a user to a provider's site or store and to enable payment for products and services delivered by the provider to the user. The terms and conditions for taking a user's personal and financial data as described above typically include some promise by the provider to securely store, handle and maintain the user's data according to certain standards of care.

Failure to properly secure users' PII can have costly and embarrassing consequences for the provider who loses or compromises the integrity of its users' PII. For example, an online retailer who causes the loss of sensitive consumer personal or financial data through negligence or by failing to adequately protect it from criminal activity can face civil and criminal action and face restitution claims by the injured users who entrusted the provider with their PII.

It is therefore clear that best practices and technology for securing, storing and accessing sensitive user information is necessary to enable the kinds of transactions and relationships becoming the norm in our networked society. Providers who cannot reliably collect and store and deliver access to sensitive user data cannot compete and may not lawfully participate in sensitive online financial, retail, medical, governmental and other operations offered to consumers and client organizations.

Present systems and methods for keeping sensitive user data generally involve storing the user data in a secure database or electronic data structure. The secure database is assumed to prevent access to the sensitive data by anyone other than the provider's authorized administrator of the database. Secure databases include databases of user information that are encrypted using passwords only available to said authorized administrators. However, even encrypted databases can be compromised by dedicated and/or skilled attacks by criminals, or by negligence on the part of the database administrator.

Once compromised, a database can expose a vast amount of sensitive information of the provider and its users. As an example, a hacked customer database can cause the unlawful release of millions of customer records into the hands of unauthorized persons who can then use the information to fraudulently make purchases in the name of the original customers, sell the sensitive data without the permission of its owners, and so on. An analogy to conventional secure customer databases is to consider a vault that contains a large amount of valuables therein belonging to many users who entrusted the provider of the vault with their personal and financial data. An illegal release of the key or combination to the vault will thus result in the complete loss of the contents of the vault, injuring all those whose property is kept in the vault.

Furthermore, even when not compromised, current methods for storing and accessing large databases of sensitive data are inefficient and costly to their providers because they require an undue amount of computer resources to maintain and operate. In one aspect, the conventional secure database needs to be unencrypted in its entirety to permit access to any portion thereof or to permit any search of the database's contents (which cannot be searched when the database is encrypted). Accordingly, conventional systems need to unencrypt whole large data sets or records, which is computationally difficult, in order to conduct transactions on the data in the database or to search the database.

FIG. 1 illustrates a simplified arrangement for storing and accessing sensitive data in a secure database according to the prior art. Database 100 is presumably secured by an encryption scheme requiring a key 120 to unlock or unencrypt the database 100. The key 120 is only held by the manager of the database or the manager's designees and is presumed secure from unauthorized access.

Sensitive data or PII 110 is kept as a data record, table or similar data store in database 100. Examples of PII stored in the database 100 includes a user's first and last names 112, 113; the user's date of birth (DOB) 111; the user's home address 116; telephone number 115; Social Security Number (SSN) 114; email address 117; credit card information 118; etc. It is clear that a user does not wish this sensitive information about him or her to be made public or fall into the hands of unauthorized users. Many users 120 (e.g., all of the customers of a bank or retail store) have their data in database 100. Therefore, the encryption key 120 is the conventional system's primary way to avoid unwanted loss of sensitive data 110. The full table of PII 110 must be accessed and unencrypted each time any information from the database is to be retrieved or searched.

FIG. 2 illustrates a conventional database 20. The database 20 is typically a monolithic computer data structure, file, or similar record stored in a secure memory storage device and contains personally identifying information (PII) for a plurality N of users or members of a group such as customers of a retail store. Each user U1, U2, . . . , UN has a corresponding user record or user file 200, 210, . . . , 220 associated therewith. Each record or file 200, 210, 220 of the users U1, U2, UN contains a plurality of PII. For example, for each respective user the user's first name, last name, street address, town, state, zip code, phone number, date of birth, social security number, membership ID number, credit card numbers, bank account numbers, or any other PII including custom or proprietary PII characterizing the user can be included. We indicate a first PII of a first user as U1.PII1; a second PII of the first user as U1.PII2; a third PII of the Nth user as UN.PII3; and so on. In this configuration, the database 20 is stored and accessed as a whole, requiring the entire database 20 to be made available to anyone reading, writing or searching its contents. The entire database 20 is encrypted and unencrypted to secure and to access the database 20. A compromise of the encryption key for encrypting database 20 would therefor result in the compromise of all of its contents. An unauthorized person who unencrypts and accesses database 20 could see all of the stored PII for the users U1, U2, . . . , UN, thereby injuring the privacy and security of each of the user members of the database 20. Furthermore, if the number of PIIs 202 kept in the database 20 or the number of users N becomes large, the computational effort and cost required to constantly lock (encrypt) and unlock (unencrypt) database 20 becomes unreasonably large. Distributing database 20 and its encryption key among administrators of the database increases the likelihood of loss of the contents of database 20.

Improved systems and methods for collecting, storing and accessing sensitive data are required. Not only is the confidentiality and security of the information a current issue, but the speed and costliness of the operation of such systems are as well. The following disclosure provides such systems and methods, including preferred embodiments detailing exemplary operations thereof, which can be used in a large number of applications. The benefits of the following systems and methods are applicable to industry, commerce, health care, government, education and other fields.

SUMMARY

An embodiment of the present invention is directed to a method for storing and accessing personally identifying information (PII) including a plurality of type fields of PII, comprising collecting a plurality of PII data relating to a plurality of fields of PII for each user of a plurality of users, for each collected PII datum and for each of said users and for each type field of PII collected, associating a unique code with said PII datum so as to create unique data pairs, each data pair comprising said PII datum and its associated unique code, for each of said type fields of PII collected, storing said data pairs relating to a PII datum in said type field of PII in respective separate data stores so that the data pairs for the plurality of type fields of PII are not all stored in a same data store but are separated by the type field of PII to which they relate, and storing in a separate and secure data store a data structure that associates the unique codes for each PII datum that are associated with a given user once said separate and secure data store is unlocked.

Another embodiment is directed to a system including an application process coupled to a key store holding a security key (e.g., encryption key), a secure tumbler data structure requiring said security key to unlock, a vault and a bank data store. An example includes a system for storing and accessing sensitive personally identifying information (PII), comprising a first data store comprising a plurality of data pairs of a first field type, each of said data pairs of the first field type including a PII of said first field type and a corresponding unique identifying code for each of said PII of the first field type; a second data store comprising a plurality of data pairs of a second field type, different from said first field type, each of said data pairs of the second field type including a PII of said second field type and a corresponding unique identifying code for each of said PII of the second field type; and a third data store comprising associating said unique identifying codes of the first field type data pairs with said unique identifying codes of the second field type data pairs so as to permit uniquely associating the corresponding PII of said first types with the corresponding PII of said second types.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

The present disclosure is directed to systems and methods for securely and efficiently storing and using personally identifying information (PII), which includes several fields of PII for a given user of a service or offering provided by a provider. Compared to brute force prior art approaches requiring encrypting and unencrypting large databases of user PII (e.g., databases of customer personal and financial data) the present systems and methods are more secure and are more computationally efficient.

In an aspect, the present invention pairs each piece of PII data with a corresponding globally unique identification (GUID) code associated with that piece of PII data. The GUID may be a random number of a certain form or length associated with a given piece of PII data. This piece of PII data and its associated GUID code form a data pair. In another aspect, the present invention divides the storage of the (PII:GUID) data pairs into separate data stores, each data store containing information relating to a separate field of PII. In yet another aspect, the invention stores a secure table or tumbler means that permits association of the various GUID codes of a user so that the system can search for PII of a user based on a criterion.

Figure 3:
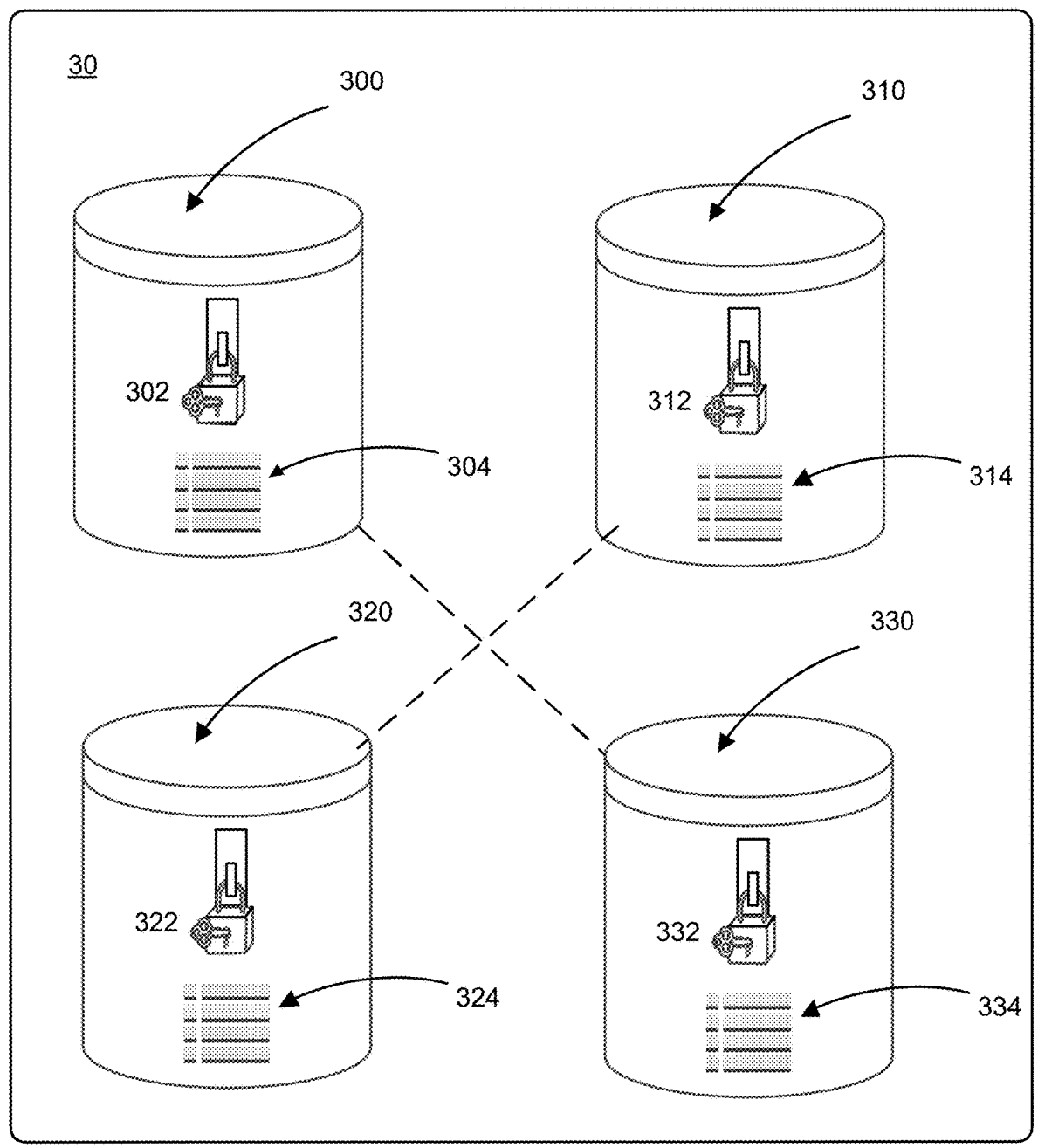
FIG. 3 illustrates corresponding sets of personally identifying information (PII) and GUIDs for a plurality of users.

FIG. 3 illustrates an architecture 30 for storing and accessing PII according to the present invention. A plurality of databases or data structures (generally data stores) 300, 310, 320 and 330 store a corresponding plurality of PII fields of different types for the same group of users. The data stores 300, 310, 320 and 330 may be represented as each being locked or secured by an encryption key 302, 312 322 and 332 respectively, but the securement of each of the separate data stores is optional and can be flexibly customized per data store to suit a given need. For example, data store 300 can store a name field PII 304 of a set of users; data store 310 can store a telephone number field PII 314 for the set of users; data store 320 can store a credit card number field PII 324 for the set of users; and data store 330 can store a date of birth field PII 334 for the set of users. More data stores can be included in the system 30. However, the data stores while being able to be kept physically or logically separated are accessible by the system as needed. We now examine the way in which data is kept in the data stores 300, 310, 320, 330 of the present example.

Figure 4:
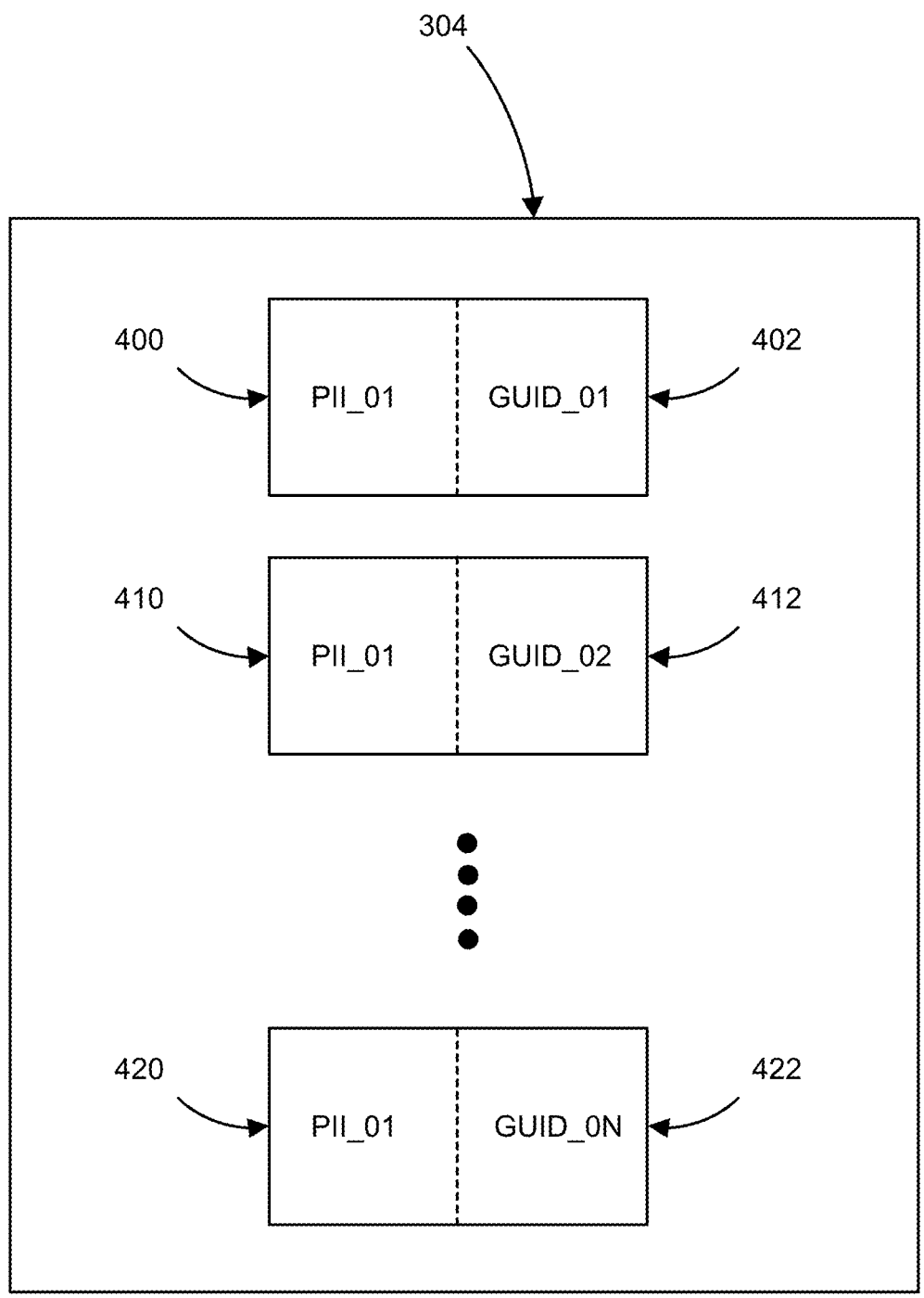
FIGS. 4 and 5 illustrate exemplary data pairs of PII and GUIDs.

FIG. 4 illustrates one of the PII field groups 304 of one of the above data stores 300, which can for example be a user "name" field PII. The PII fields may be broken down into sub-fields as desired, and the sub-fields may be separated into discrete data stores or combined into a same data store, depending on the application at hand and the level of security desired. So, for example, the user or customer name may be kept in a same store including both first and last names, or it may be kept separately in two stores, one containing first names and the another containing last names. But the name(s) and other PII fields or sub-fields are separately stored in different databases or data structures accessible to the provider or owner of the database system.

Figure 1:
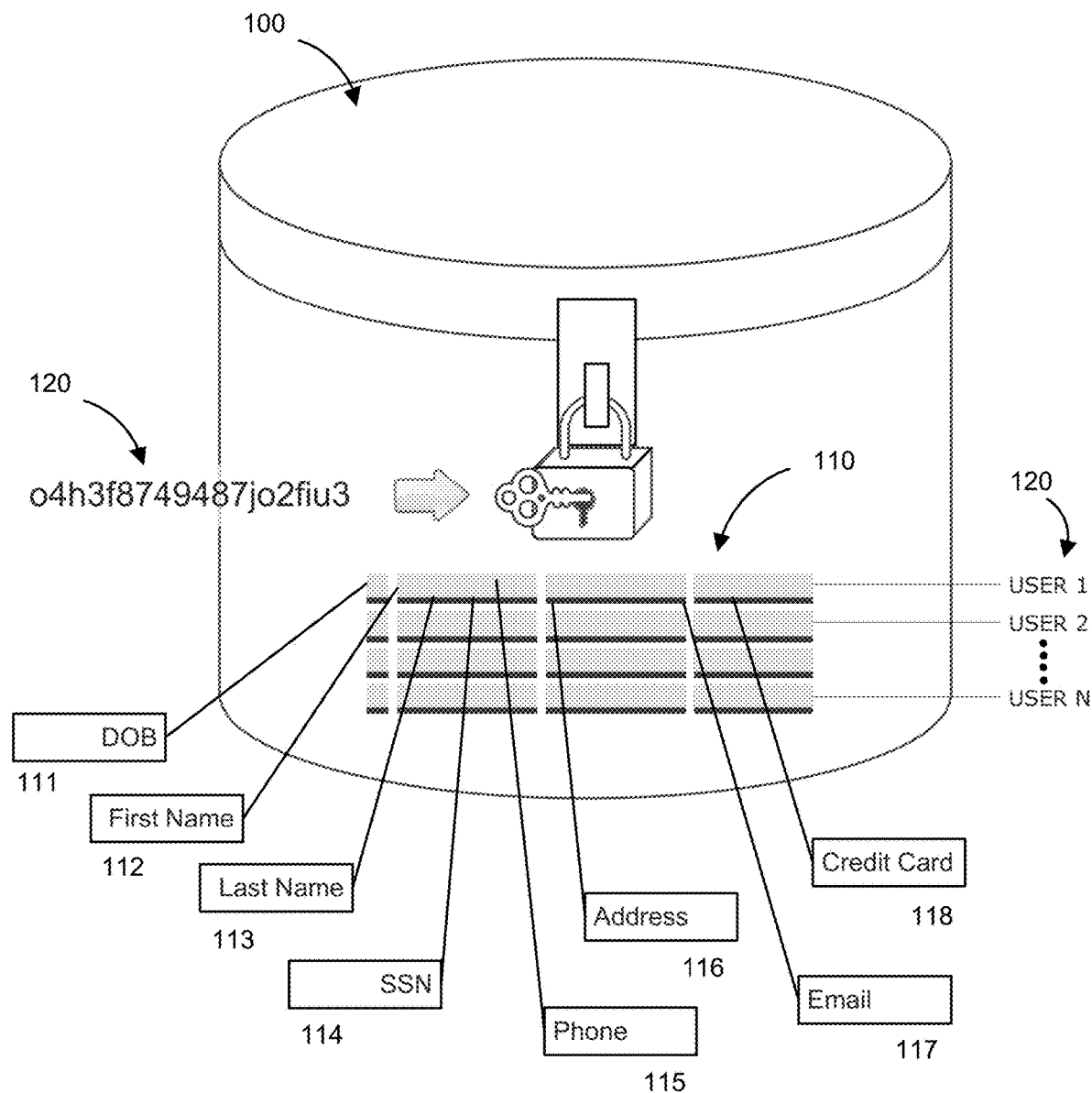
FIG. 1 illustrates a conventional encrypted database of information.
Figure 2:
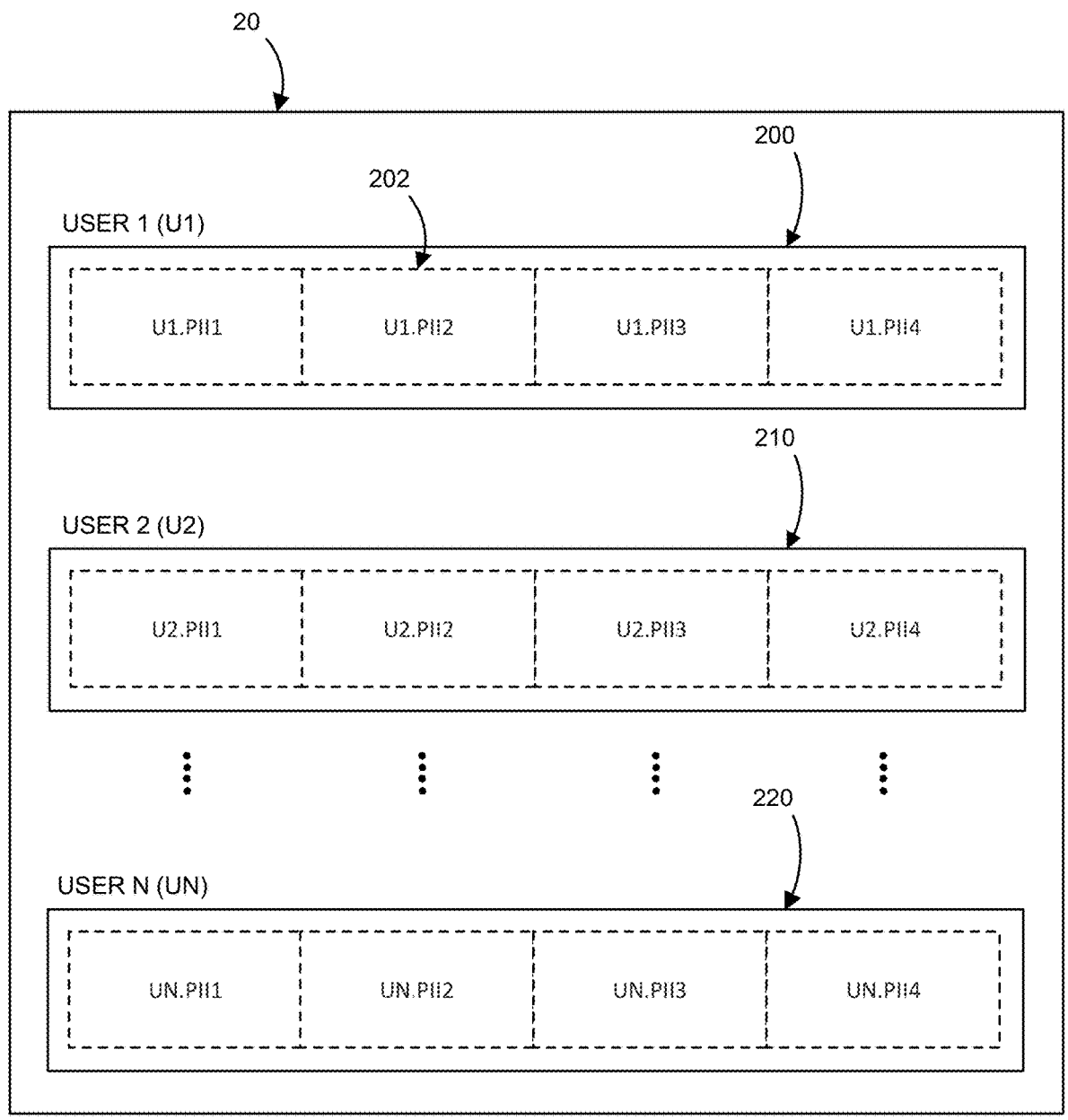
FIG. 2 illustrates a conventional database of several users each having a record containing several pieces of personally identifying information (PII)

A security advantage of this architecture is that negligent or malicious cracking (unlocking) of one data store would only expose one field of PII (e.g., names but not other data; or phone numbers but not other data; or social security numbers but not other data; and so on). This is a security advance because unlock traditional secure databases as in FIG. 1 the present system does not provide access to all PII type fields for any users even if one of the data stores of FIG. 3 is compromised. In fact, if some data in one or more stores of system 30 is not very sensitive it may not need to be encrypted and could even be stored as clear text or plain data. For example, type fields such as zip codes, employer addresses, length of time at current residence, or dates of birth, that taken without other PII information are of little value and may not need to be stored in locked data stores. Storing non-sensitive data type fields like this could speed the access time and search time, as encrypting and decrypting data requires costly computing resources better used for other purposes. Specifically, by leaving certain types of PII unencrypted in their data stores, the present system and method would facilitate easier searching with lower computational requirements than searching a data store which is encrypted. More specifically, in an embodiment where one or more PII are not encrypted in their data stores, this method and system could easily perform generalized (e.g., wildcard) searching such as a search for "Da*" which would capture "Dave", "David" and other matching results. This type of searching is not possible, or is much more complicated and costly in searching encrypted data store contents.

The PII field group 304 of FIG. 4 (for example, the users' first name field represented at PII_01) includes a plurality of data pairs whereby a PII information type field for a user is paired with a distinct identifying number or code (GUID) to make a distinct PII-GUID data pair. For example, a data pair includes the PII field 400 and the GUID 402. In this example, the pairs include PII_01:GUID_01; PII_01: GUID_02; . . . PII_01:GUID_0N, which may represent the first name (PII_01) and its associated GUID_01 402 for a first user. Another data pair is PII_01 410 and GUID_02 412 representing a second user's first name (PII_01) and its associated GUID_02 412.

Figure 5:
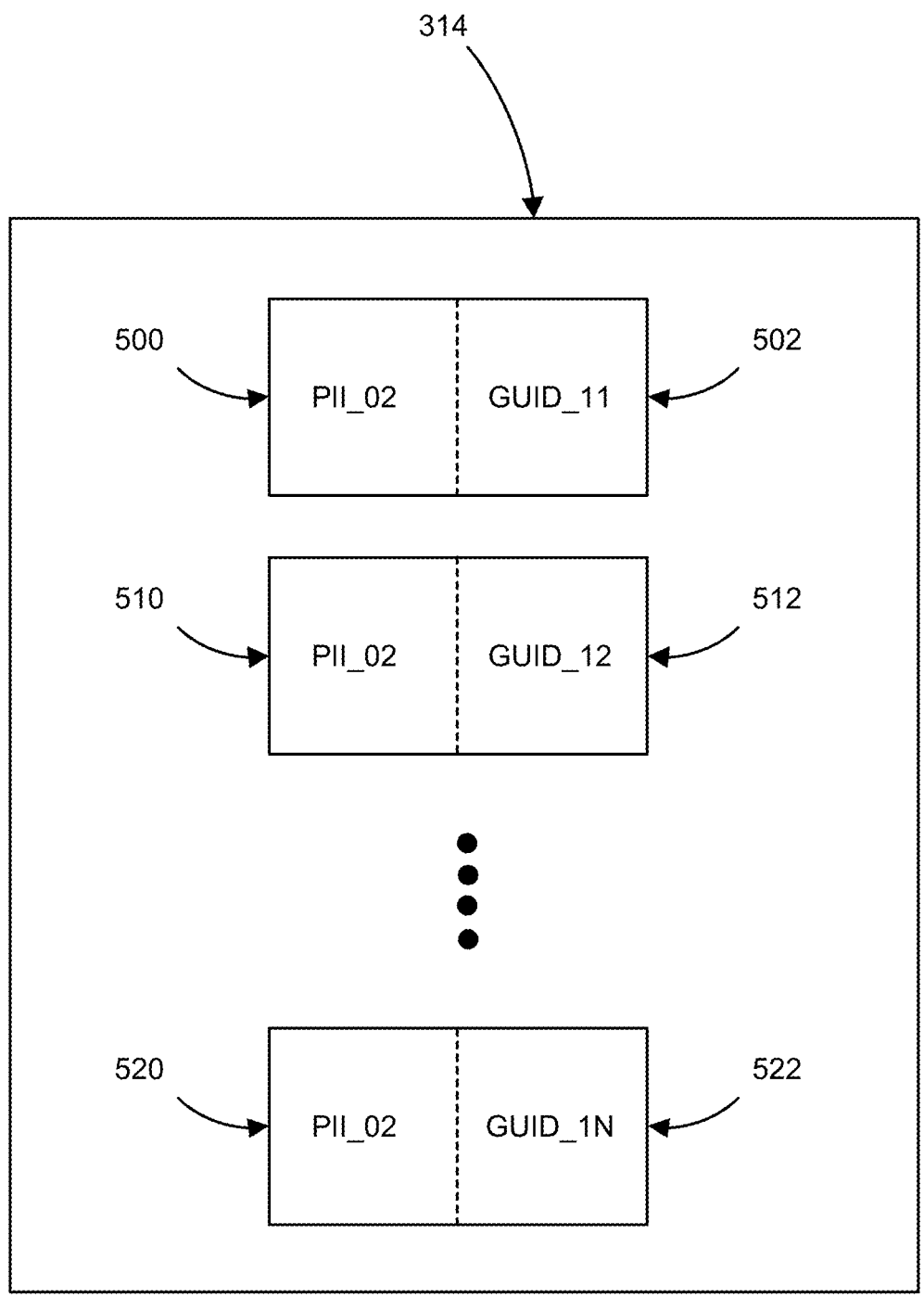

Continuing this example, the PII field group 314 (for example, the users' dates of birth PII_02) having for each user a data pair including the date of birth date data itself PII_02 for a user and an associated GUID for that data for that user. The PII field group 314 in FIG. 5 includes a data pair 500:502 representing the date of birth PII_02:GUID_11 of the first user; another data pair PII_02 510:GUID_12 representing a second user's birth date PII_02 and the second user's birth date GUID_12 512, and so on.

It should be clear now that for as many fields or sub-fields of PII data for as many users or subscribers or customers desired, any individual data entry for any user is paired with a GUID code, preferably unique to that user and PII field entry.

Since the present invention keeps the fields of PII data separated into separate data structures or databases, it is now time to describe how the present system associates the various PII fields for a given user with one another. That is, we now discuss how the system associates a given user's name, address, phone number and bank account (or other PII fields) with one another if the system's users' names are all in one store, but all of the addresses are in another store, and the phone numbers in yet another store and the bank accounts in still another store. Recall that, as shown in FIG. 3, each field of PII is stored separately in a data store. Providers (e.g., retailers, banks, healthcare providers, educational institutions) need to look up for a given user what the user's PIIs are generally and not just one field of the given user's PII, therefore merely unlocking one data store would only unlock one field of PII. Accordingly, the provider will need a method for associating several or all fields of the given user's PII with one another. For an abundance of clarity we continue our discussion in view of the examples of FIGS. 3, 4 and 5. Assume that the user names 304 are encoded in data store 300 and their birth dates in data store 310 and so on. Unencrypting data store 311 containing the set of user birth dates 314 would not tell us which birth dates 314 belonged to which user names 304, and vice versa. We present a way to associate these PII fields 304, 314 (and others 324, 334, etc.) with one another so a provider can see for a given user what the user's complete PII is. An aspect of this invention uses the GUIDs associated with each PII field of each user as a way of coupling the separately stored PII field data with one another.

In an embodiment, the present system and method include a secure data store containing the GUID codes for the various users' PII data fields and enable the system to determine which GUID codes from each of the data stores of FIG. 3 belong to a same user in the way a mechanical lock "tumbler" operates to unlock the mechanical lock when the components of the lock are tumbled by an appropriate key to fall into place revealing the whole PII picture for a given user. Once unlocked, the present tumbler system and method permit an authorized provider with access codes to the tumbler database of GUID codes to associate the correct GUID codes with one another so that the provider can see the PII data for a given user in their entirety or to the extent needed for a given application. Meaning that for example a retail provider can look up and ship to a given user his or her merchandise, using the user's correct name, address, credit card information and other data that can all be associated by way of these fields' GUIDs and that are respectively associated with the PII fields for the user as discussed above. Since the PII fields for the user are uniquely connected to their respective GUID codes, unlocking a GUID code database (tumbler) store will serve to connect the corresponding PII field data for the user with one another.

It should be appreciated that the present system and method offer computational efficiencies in addition to security advantages as mentioned above. The individual data stores of FIG. 3 are far easier to unlock separately (decrypt if encrypted) than to unlock an encrypted monolithic database like the one of FIG. 1. This is especially easy under the present method if one or more non-sensitive fields of data are stored without encrypting them in the first place. As mentioned, street address numbers alone would be of such little value to an unauthorized user as to be potentially safe to store in plain form without encryption. Birth dates are also not very interesting to malicious third parties, as any date of the year could be posted publicly and is sure to be someone's birthday, which does not give away any sensitive information about anybody. Even first names might be stored without special care for their particular obscurity because a database of first names is unlikely to compromise any or most people. It is when the separate PII fields are associated with one another (for example in knowing the name, address, and phone numbers of people) that the combined fields become of some value or risk to their owners. As mentioned before, there are computational and cost advantages to keeping at least some of the PII stored in unencrypted form so as to be able to easily search through such data, perform wildcard searching on it, etc.

Figure 6:
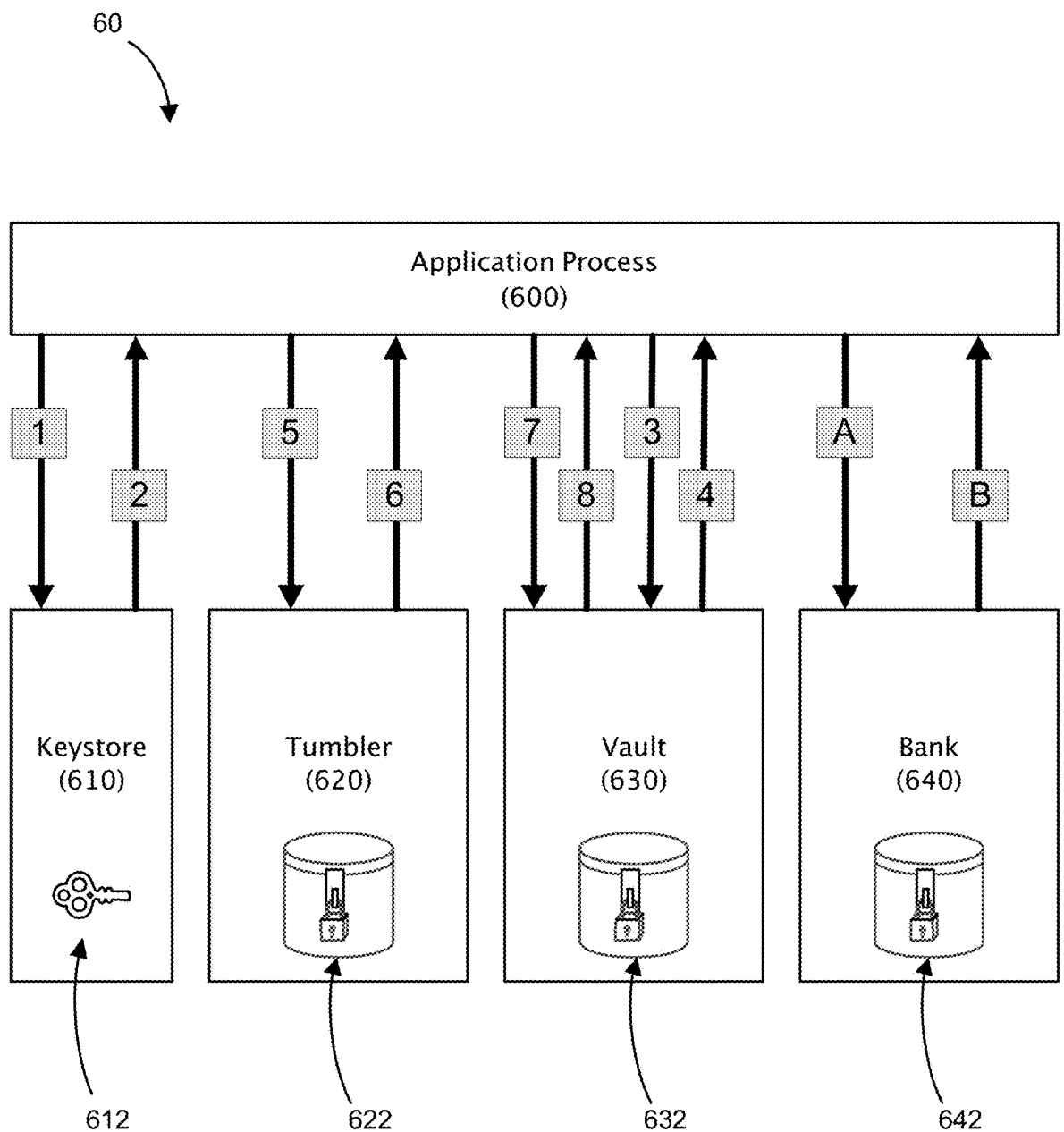
FIG. 6 illustrates an architecture according to embodiments of the present system and method.

FIG. 6 illustrates an architecture 60 according to embodiments of the present system and method. An application process 600 is configured and operated to exchange data with several components of the architecture 60. These components include a key store 610 containing encryption keys 612 or similar means for unlocking a secure (e.g., encrypted) data store. Tumbler 620 contains a persistent data store 622 in which are stored tkey:ekey pairs of data. Vault 630 contains a persistent data store 632 in which are stored data pairs ekey:VALUE and ekey:EVALUE. Also, vault 630 can include or be associated with a search index which indexes the ekey:VALUE data pairs. Bank 640 includes a persistent data store 642 holding data pairs pkey:VALUE as well as a search index which indexes data pair VALUE:pkey.

Therefore, the application process 600 can store and retrieve encryption or security keys 612 in key store 610. These keys are used to unlock the tumbler 620 and therefore reveal the associations between the GUID codes corresponding to the PII fields of a user so that the user's PII are generally unlocked upon demand by an authorized provider.

In an embodiment, the "ekey" can be an encrypted code, which is encrypted using the "tkey" as its encryption key. The PII data shown at FIGS. 8, 9, 10 may have different "ekey" assignments to the various PII associated with a given user so that if these data are compromised it is not obvious which user the data relate to. Meaning, in an embodiment, the same user's Name, Phone, Email, Address, etc. each have a different encrypted "ekey" that are derived from encrypting a same "tkey". The "tkey" being the thing that connects the relationships between the various encryption results for that given user's PII and their respective encrypted ekeys. As will be discussed below, by encrypting the "ekeys" there is no easy way for unauthorized persons to determine which "ekeys" for which PII pieces belong to one another without the "Tumbler" key ("tkey") to tell the system which "ekeys" belong with one another.

Therefore, the "ekeys" can be encrypted (either in a PII data store or in the Tumbler), which will avoid unwanted exposure of the connectedness of the associated PII by anyone not in possession of the instant Tumbler key.

Referring to the shaded boxes representing information passing between the components of system 60, these represent exemplary steps of communicating information according to an exemplary embodiment for using the system 60. In step 1 the Application Process 600 makes a call to the Keystore 610 to request encryption keys for a given customer. If the Application Process' request is authentic, Keystore 610 returns the requested encryption key 612 to the Application Process 600. The Application Process 600 takes the provided encryption key 612 and uses this to access secure Vault 630, which contains a data store 632 having PII information for a user or users who are the subject of a given query at step 3.

Once information matching a query are found, the PII: GUID data pairs and information from vault store 632 matching the query are returned from Vault 630 to Application Process 600 at step 4. The PII retrieved by the Application Process 600 from the Vault store 632 can include results of a query for a certain name, address, age, bank account information and other PII, which are returned to the Application Process 600 along with the corresponding GUID codes for each of these pieces of PII as described above with respect to FIGS. 4 and 5.

A query may for example call for all of the customers of a certain merchant whose first names are "Dave" and whose address includes "Seattle." As noted before, this information alone, even if it were to fall into the wrong hands, is of little value as many people are called Dave and many addresses contain the word Seattle. Even where other PII such as social security numbers are exposed, they remain reasonably harmless because at this stage the information is just in raw format and is not sorted or arranged so that an unauthorized person could determine which Dave lived at which Seattle address and had which bank account, and so on. That organization to sort the pieces of discrete PII into same-person rows is done next by the Tumbler 620 component.

Now the system 60 sends all of the PII information and GUID code data pairs retrieved from Vault data store 630 to Tumbler 620 for sorting into meaningful data sets associated with particular users. Tumbler 620 has a Tumbler store 622 which holds in it the keys to unlocking, analogous to the tumbler of a mechanical lock, the match between various PII information using the PII:GUID data pairs of the information. So using our mechanical analogy only to the limited extent of this statement, the Tumbler 620 can identify the GUID codes of the PIIs that belong to the same set of PII associated with a given user. The Tumbler 620 acts as the unscrambling element that can sort the scrambled PII information into meaningful sets so that the operator can then see in response to its query what the proper name, address, phone number, bank account number, age and other PII of a given user. This sorted set of PII is returned at step 6 to the Application Process 600 and the operator of the process can intelligibly see the sorted PII information for users named "Dave" living at "Seattle" in the previous example.

The Bank 640 contains a Bank data store 642, which holds other information relating to a customer, user, transaction or any other data that can be associated with the query, but is not necessarily of a highly sensitive nature. For example, the Bank store 642 could hold offers, discount codes or other electronic files, images or articles of commerce usable by Application Process 600 in the course of its operation. Steps A and B represent requests and replies to and from Bank 640. The Bank 640 is not a necessary component of all embodiments of the present invention. Likewise, one or more of the above components can be implemented by those skilled in the art differently from that described in the present illustrative examples. The arrangement and keeping and architecture of the components of FIG. 6 can be kept as most suitable for a given operator of the system 60.

In an aspect, the Keystore 620 is a single-tenant multi-instance component, the Tumbler 620 is a single-tenant multi-instance component, the Vault 630 is a multi-tenant single-instance component, and the Bank 640 is a multi-tenant single-instance component. By single-tenant it is meant that a single customer's data is kept in the data store. Multi-tenant means multiple customers' data can be kept in the data store. For very sensitive information such as the Keystore encryption keys, system 60 may implement the system as a single-tenant Keystore 610 for added security. However, the Vault 630 might in an embodiment be a multi-tenant component so as to keep the information from the users of more than one customer of the system 60. For example, if the system 60 is operated by its owner/operator to service a plurality of online retailers, each of which is a customer of the operator of system 60, there are normally a large number of users of each of these tenants/customers. So a single-tenant component in this instance means a data store (e.g., 612) that is dedicated to the users of a single tenant/customer of system 60. Multi-tenant components (e.g., Vault 630) can be split into more single-tenant components or into a plurality of other smaller multi-tenant components as desired. Having a multi-tenant component (e.g., Vault 630) allows the system 60 to scale up to very large data stores containing a large amount of information. In an aspect, having more data in the data stores of system 60 reduces the significance and risk of exposure of any one or few or several pieces of PII.

By multi-instance it is meant that there is a plurality (usually many) pieces of data stored in a component, even if the component is single-tenant. So for example the phone numbers of a large number of customers of an online retailer can be stored in a multi-instance data store component.

The architecture of exemplary FIGS. 3 and 6 could be implemented so that there is no direct connection between one data store and the next. For example, referring to FIG. 6, the system may be implemented so that the data stores or modules 610, 620, 630, 640 are substantially isolated from one another and only relay information to and from the application process 600. This can increase the security of the system 60 so as to minimize the likelihood of global loss of the PII:GUID data pairs and the likelihood of compromising the owners of that information. Furthermore, this allows the manager of the system to monitor its operation to avoid misuse of the system.

Figure 7:
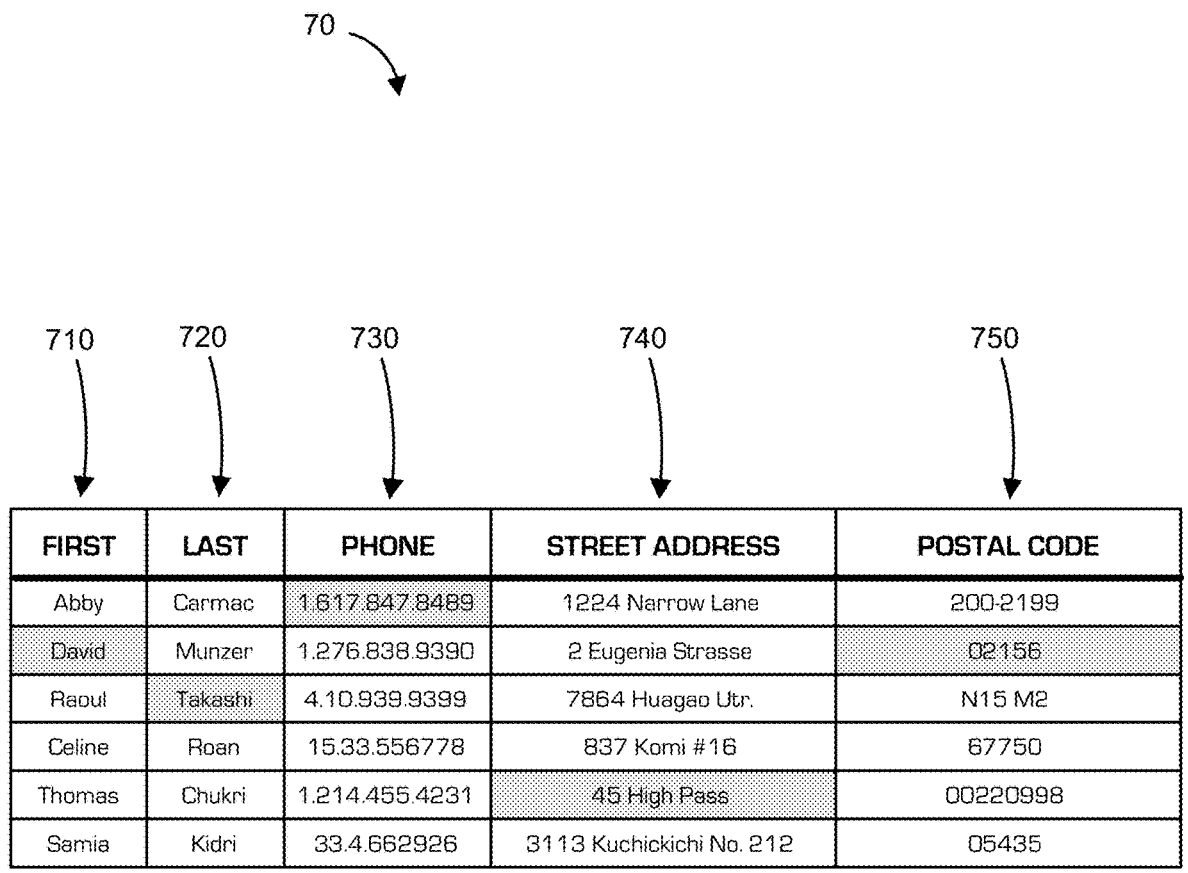
FIG. 7 illustrates various PII of different field types for a plurality of users.

FIG. 7 illustrates a table 70 of some personal information relating to a plurality of users (for example shoppers of an online retailer). Obviously this is given as a simplified example and in use the table may include much more information, for example financial data and other personal data for each user. The information can be visualized as being tabular and in column and row format, but those skilled in the art will appreciate that a data structure can be of other formats and can be multi-dimensional and can be in any representation that suits a given purpose and computer architecture. For illustration, we depict several columns of PII data such as First name 710, Last name 720, Phone number 730, Street address 740, and Postal code 750.

Note that the pieces of PII can be scrambled and require sorting so as to arrange the pieces of PII properly to correspond with a particular user. In this example, we show shaded blocks indicating a user named David Takashi whose phone number is 1.617.847.8489 and whose street address includes 45 High Pass and whose postal code is 02156. However, these pieces of PII are not generally stored in an organized form in a database so that if the database is compromised there is no clear way to know which pieces of PII belong to which other pieces. By associating each piece of PII with a unique GUID in a PII:GUID pair and using the present system and method, including the Tumbler described herein, it is possible to properly sort and associate the various pieces of PII into a meaningful search result (e.g., for a person named David having a postal code 02156, and so on).

Figure 8:
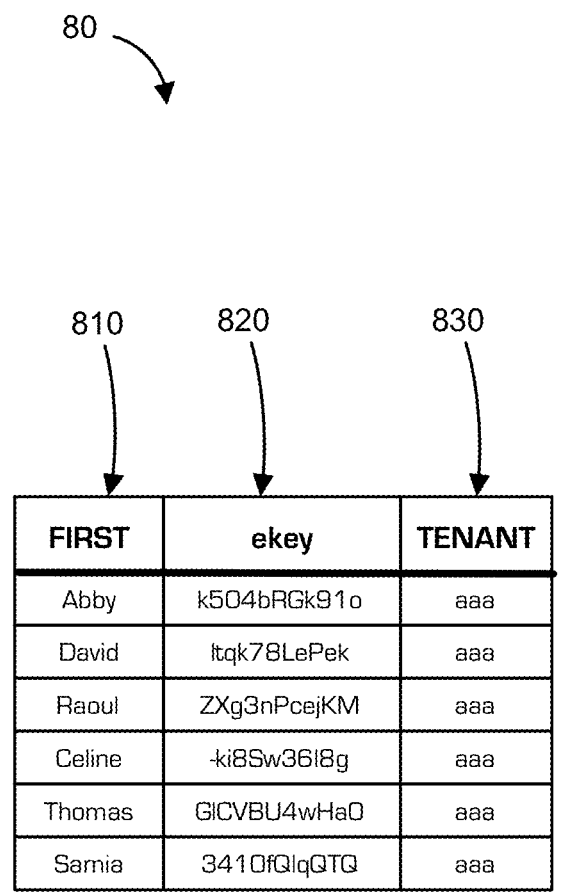
FIG. 8 illustrates contents of a data store containing First name information and uniquely identifying GUID codes.

FIG. 8 illustrates how a data pair of a piece of PII and its unique associated GUID are kept according to an embodiment. These data pairs comprising PII:GUID are generally kept in a table 80 and kept in a data store which can be secured to further prevent unwanted disclosure. In addition, the table 80 stores the Tenant 830, which for example in this query is "aaa." The Tumbler component described above will use the GUID 820 (also herein "ekey") associated with a given piece of PII 810 to associate the PII of a given user or query subject together.

Figure 9:
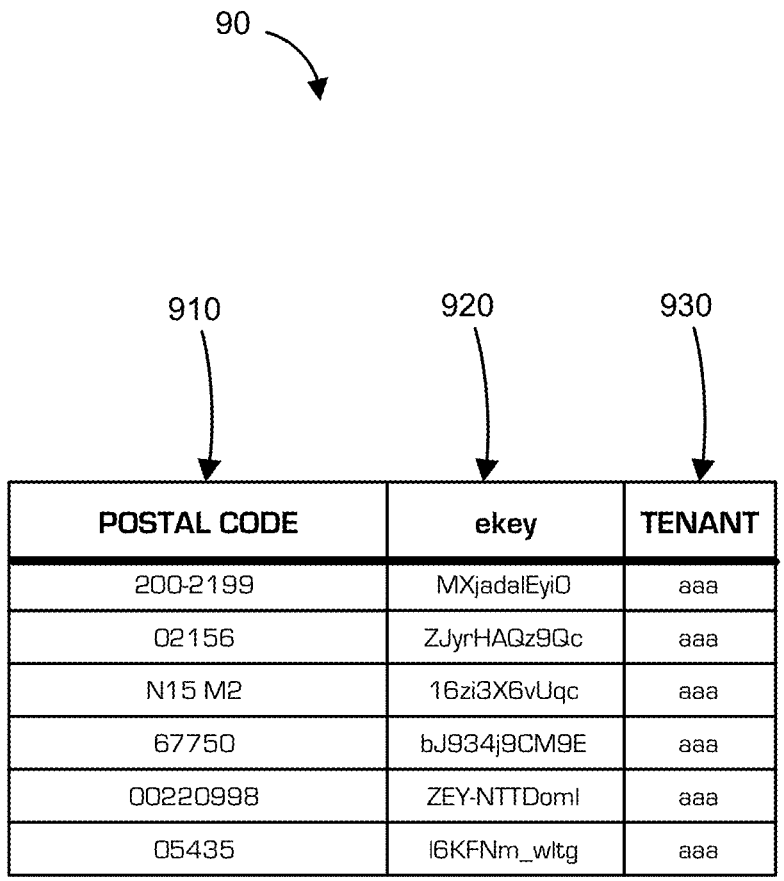
FIG. 9 illustrates contents of a data store containing Postal Code information and uniquely identifying GUID codes.

FIG. 9 illustrates a similar table 90 as that described above, including the Postal code 910 data and GUID that has been encrypted (e.g., ekey) 920 associated with that PII, as well as the Tenant 930 for the query in question.

Figure 10:
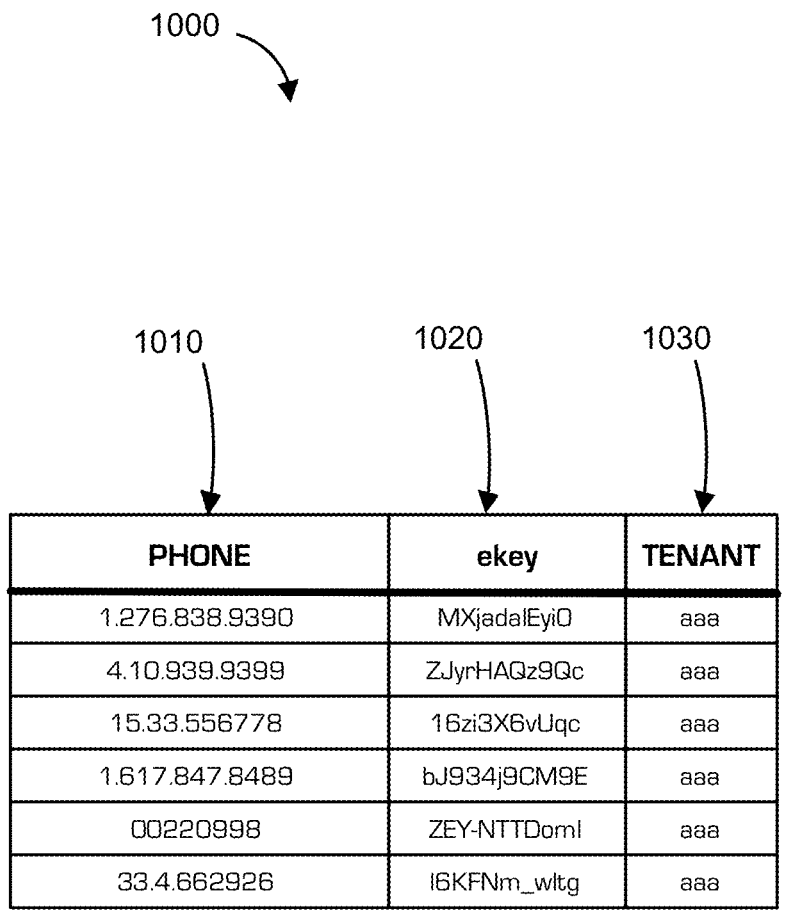
FIG. 10 illustrates contents of a data store containing Phone numbers and uniquely identifying GUID codes.

FIG. 10 illustrates another table 1000 as that described above, including a Phone number 1010 and its unique GUID that has been encrypted (e.g., ekey) 1020 and Tenant ID 1030. Such tables or data structures can be made for each or subsets of each type of PII.

Figure 11:
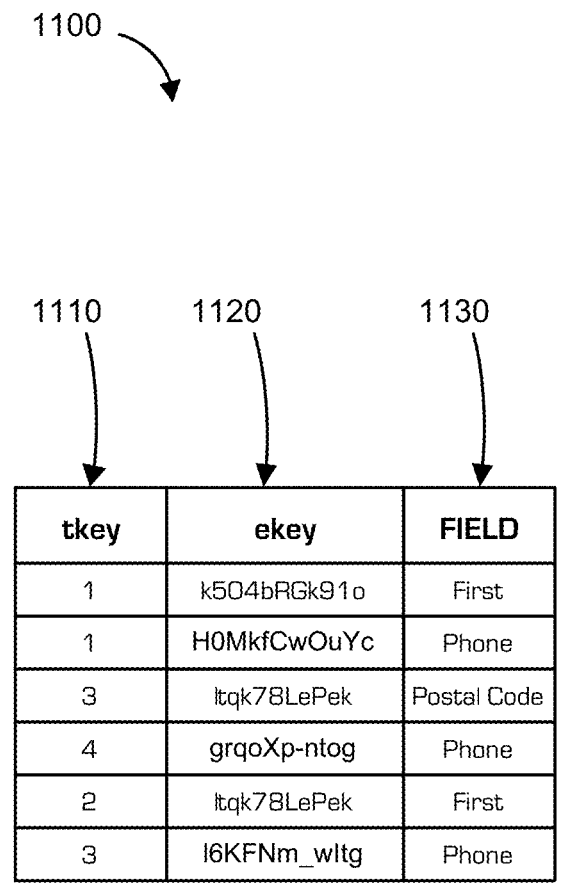
FIG. 11 illustrates contents of a "Tumbler" data store associating GUID codes of various field types with one another.

FIG. 11 illustrates the contents of a Tumbler data store 1100 like those described earlier. A Tumbler key or "tkey" 1110 is associated with a given GUID or "ekey" 1120 and a "Field" 1130 representing the type field of the PII. So the types of PII "First" (FIG. 8), "Postal Code" (FIG. 9) and "Phone" (FIG. 10) are referred to as a type fields of PII for the present purpose.

In one aspect, the "tkey" above can be analogized to a row in a spreadsheet with each piece of PII sharing a same "tkey" for any given data record for a user. Therefore, if two pieces of PII share a same "tkey" it would be understood that these two pieces of PII belong in the same data record for the user. Therefore, since the associated "ekeys" for the ekey:PII data pairs are encrypted (either in the PII datastore or in the Tumbler datastore) there is no way to elucidate that the two pieces of PII are part of the same record without authorization (by way of the Tumbler "tkey" acting as a row ID in the above analogy).

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method for computer storage and access of personally identifying information (PII) including a plurality of fields of PII, comprising:

collecting a plurality of PII data relating to a plurality of respective fields of PII for each user of a plurality of users;

associating a unique identifying code with each said PII datum for each said field of PII so as to create unique data pairs, each data pair comprising said PII datum and its associated unique identifying code, where each unique identifying code is a globally unique identification (GUID) that is unique to the field of PII to which that PII datum belongs and to the user to which that PII datum relates;

storing said data pairs in one or more computer data stores without organization from which can be determined which data pairs comprising PII data for a given user belong to which other data pairs for that same user;

securing in a further separate computer data store a data structure that associates with each said user the unique identifying codes of the data pairs that comprise PII data for that user;

subjecting the PII data in the one or more computer data stores to one or more queries;

returning data pairs from the one or more computer data stores matching the one or more queries, where those returned data pairs (i) comprise PII data for a plurality of said users, (ii) are without organization from which can be determined which data pairs comprising PII data for a given user belong to which other data pairs for that same user; and utilizing the further separate computer data store to identify, from the unique identifying codes in the returned data pairs, which PII data for a given user in those returned data pairs belongs to which other PII data in those returned data pairs for that same user.

2. The method of claim 1, further comprising unlocking said further separate computer data store so as to identify unique identifying codes for a given said user.

3. The method of claim 2, wherein the further separate computer data store is encrypted with a key that differs for a key with which one or more of the data stores in which data pairs are stored is encrypted.

4. The method of claim 1, wherein the step of storing data pairs in one or more computer data stores further comprises storing data pairs having PII data relating to at least one field of PII in a said computer data store that is separate from a said computer data store in which data pairs having PII data relating to at least one other field of PII are stored.

5. A computer storage and access system for storing and accessing sensitive personally identifying information (PII) data for a plurality of users, comprising:

a first computer data store storing a plurality of data pairs of a first field type, each of said data pairs of the first field type including a PII datum of said first field type for a respective user and a corresponding unique identifying code for that datum and user, where each unique identifying code is a globally unique identification (GUID) that is unique to the field of PII to which that datum belongs and to that user;

a second computer data store storing a plurality of data pairs of a second field type, different from said first field type, each of said data pairs of the second field type including a PII datum of said second field type for a respective user and a corresponding unique identifying code for that datum and user, where each unique identifying code is a globally unique identification (GUID) that is unique to the field of PII to which that datum belongs and to that user; and a third computer data store storing a plurality of data structures associating said unique identifying codes of the first field type data pairs with said unique identifying codes of the second field type data pairs so as to permit uniquely associating the corresponding PII datum of said first type with the corresponding PII datum of said second type for a said respective user subjecting the PII data in the first and second computer data stores to one or more queries;

returning data pairs from the first and second computer data stores matching the one or more queries, where those returned data pairs (i) comprise PII data for a plurality of said users, (ii) are without organization from which can be determined which data pairs comprising PII data for a given user belong to which other data pairs for that same user; and utilizing the third computer data store to identify, from the unique identifying codes in the returned data pairs, which PII data for a given user in those returned data pairs belongs to which other PII data in those returned data pairs for that same user.

* * * * *